United States Patent [19]

Tsuk

[11] 4,153,052

[45] May 8, 1979

[54] ORTHOPEDIC CAST PACKAGE

[75] Inventor: Andrew G. Tsuk, Plattsburgh Clinton, N.Y.

[73] Assignee: American Home Products Corporation, New York, N.Y.

[21] Appl. No.: 826,277

[22] Filed: Aug. 22, 1977

Related U.S. Application Data

[63] Continuation-in-part of Ser. No. 737,944, Nov. 2, 1976, abandoned.

[51] Int. Cl.² .............. A61F 13/04; B65D 77/04; B65D 85/676; A61L 15/07
[52] U.S. Cl. ................................... 128/90; 206/389; 206/440
[58] Field of Search .................. 128/90; 134/138, 139, 134/147; 206/219, 389, 440; 242/68.5, 118, 118.1, 118.11, 118.2, 118.3, 118.31, 118.32

[56] References Cited

U.S. PATENT DOCUMENTS

| 853,236 | 5/1907 | Goss et al. ............................. 206/18 |
| 1,839,184 | 10/1930 | Kircher ........................ 242/118.32 |
| 3,027,336 | 3/1962 | Gotz et al. ......................... 128/90 X |
| 3,630,194 | 12/1971 | Boardman ............................. 128/90 |
| 3,683,903 | 8/1972 | Fox et al. ............................. 128/90 |
| 3,882,857 | 5/1975 | Woodall ................................. 128/90 |
| 3,968,791 | 7/1976 | Forsberg ............................... 128/90 |
| 4,020,832 | 5/1977 | Kirkpatrick et al. .................. 128/90 |

Primary Examiner—Robert W. Michell
Assistant Examiner—Arthur S. Rose
Attorney, Agent, or Firm—Adley F. Mandel

[57] ABSTRACT

An orthopedic cast package is disclosed comprised of a vapor-proof container having disposed therein a smaller cylindrical role of orthopedic tape wetted with a solution of a thermoplastic polymer in a non-toxic volatile solvent having a polymer concentration of at least about 20% by weight. The tape roll is disposed in a spaced relationship away from the sides and bottom of the container which is opened at the top.

14 Claims, 12 Drawing Figures

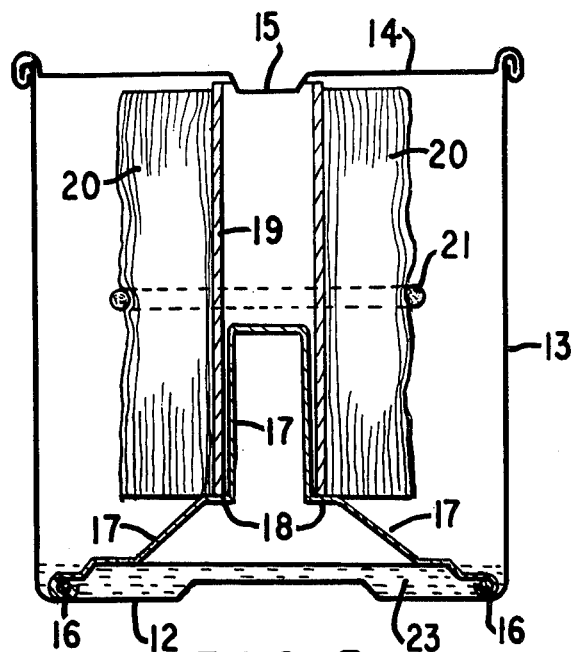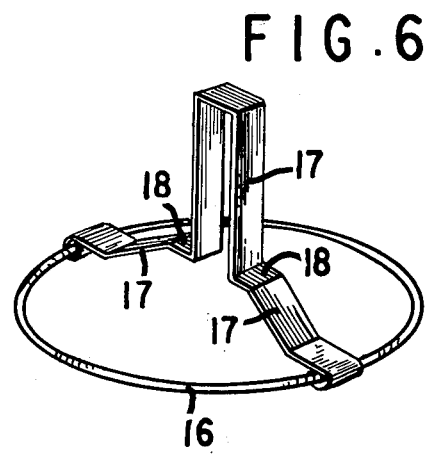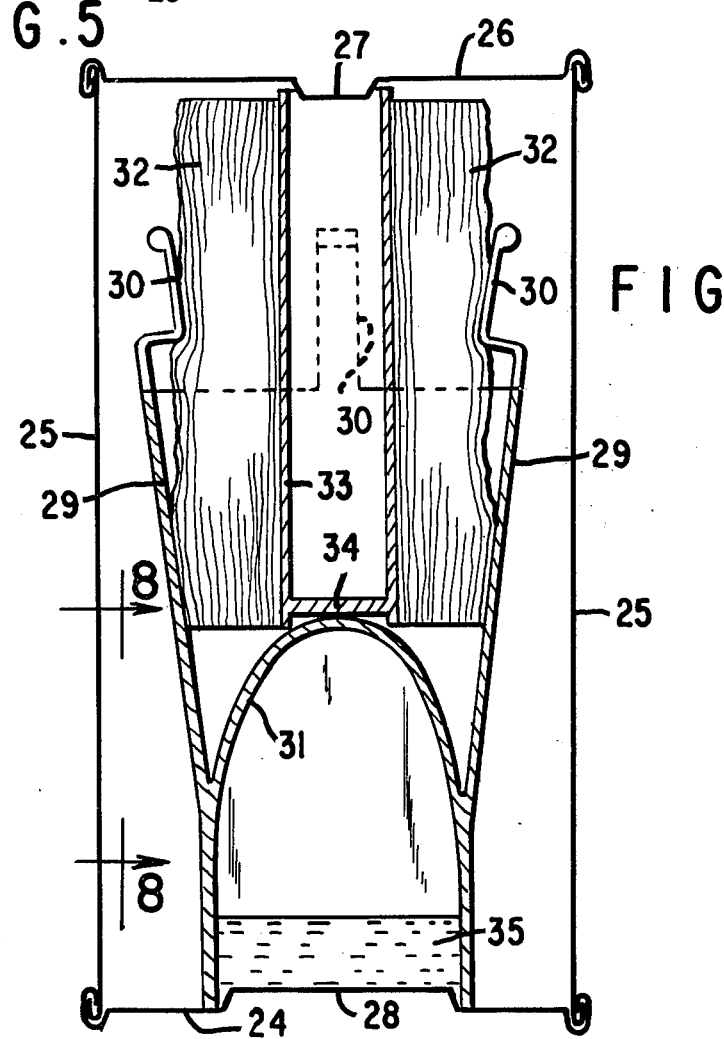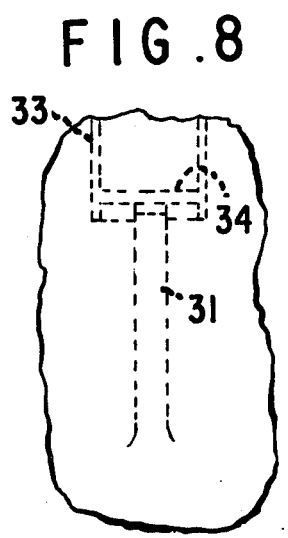

ORTHOPEDIC CAST PACKAGE

This is a continuation-in-part of Ser. No. 737,944, filed 11-2-76 now abandoned.

BACKGROUND OF THE INVENTION

The presently most widely used orthopedic cast material is plaster of Paris but recently the art has progressed to provide orthopedic cast materials that are lighter, breathable, impervious to water so as to permit bathing, and which provide clearer X-Ray results. Such orthopedic cast materials are exemplified by U.S. Pat. Nos. 3,882,857, issued May 13, 1975; 3,630,194, issued Dec. 28, 1971 and 3,968,791 issued July 13, 1976 all of which describe dry orthopedic bandages impregnated with polymerizable materials and initiators which are wetted at the point of use to initiate polymerization or which are cured by exposure to ultraviolet light. Yet another orthopedic cast system employs a dry orthopedic bandage comprising a combination of fiberglass and thermoplastic yarns, which bandage is softened by immersion in a volatile solvent, and hardens upon evaporation of same. In addition to the inconvenience and hazards of the dipping step, the setting time is not fast enough unless the evaporation is assisted by a hot-air blower.

DESCRIPTION OF THE INVENTION

The orthopedic cast system of the present invention provides a wetted bandage packaged in a vapor-proof container ready for instant application and without resort to external means for effecting polymerization of a strength-forming cast material. The bandage of the present orthopedic cast system is impregnated with a solution of a preformed polymer so that curing is effected by vaporization of the solvent. Accordingly the solution impregnated bandage is packaged in a vapor-proof container. Unlike the prior art systems, the system of the present invention provides the following advantages: the system is ready-to-use, with setting times comparable to plaster of Paris, needs no ancillary equipment, nor any dipping or mixing prior to use, and gives strong, lightweight, porous and water-resistant casts.

DETAILED DESCRIPTION OF THE INVENTION

The orthopedic cast package of the present invention comprises a container having a bottom wall, a peripheral side wall extending upwardly from the bottom wall and providing an open upper end of the container, and a closure and associated means for providing a vapor-tight seal on the upper end of the container. Mounted within the container is a hollow-core cylindrical roll of liquid pervious orthopedic tape having a diameters and height less than that of the container, the orthopedic tape being supported concentrically within the container and in a spaced relationship away from the bottom of the container. The orthopedic tape is wetted with a solution of a thermoplastic polymer in a non-toxic volatile solvent having a polymer concentration of at least about 20% by weight.

Advantageously the bottom wall of the outer container is separately attached to the peripheral side wall to provide a vapor-tight seal, the hollow-core cylindrical tape is wound about a tape spool closed at its lower end and the supporting means for the tape roll also defines a double funnel-like chamber having a constriction of diameter less than the diameter of the tape roll and larger than the closed lower end of the tape spool. The funnel-like chamber below the contriction can comprise about 20 to 50% of the volume of the outer container. Also advantageously the double funnel-like chamber has an open upper end of diameter slightly larger than that of the tape roll, so as to engage the lower portion of the tape roll, and resilient finger-like extensions extending upwardly further to engage the tape roll and hold it in juxtaposition with the double funnel-like chamber. Advantageously the supporting means further includes spacer means for maintaining the tape spool in a spaced relationship away from the bottom wall and the peripheral side wall.

The cylindrical roll of orthopedic liquid-pervious tape advantageously comprises interlaced glass yarns. Such tape material is commercially available and suitable tape materials are described in, for example, U.S. Pat. Nos. 3,654,056, issued Apr. 4, 1972, 3,787,272, issued Jan. 22, 1974; 3,793,686, issued Feb. 26, 1974; 3,881,473, issued May 6, 1975; and 3,882,857, issued May 13, 1975, the disclosures of which are incorporated herein by reference. Advantageously, the tape material is knitted using glass filament yarns the filaments of which have an average diameter of approximately 0.00015 inch to approximately 0.00025 inch. Such yarns are commercially available, yarns having a filament diameter of 0.00015 inch being known as B (or beta) filament yarns, those having a filament diameter of approximately 0.00018 inch being known as C filament yarns, those having a filament diameter of approximately 0.00021 inch being known as D filament yarns and those having a filament diameter of approximately 0.00025 inch being known as D-E filament yarns. It is desirable to employ the finest continuous filaments obtainable, i.e. the B filament, although they are more expensive. Yarns or glass fibers made from B, C, D and D-E filaments having strand counts of about 75 to about 900 are suitable, 75 to 450 being preferable, such strand counts indicating approximately 1632 to 204 filaments per fiber and weighing about 7500 to 90,000 yards per pound. Such glass fibers are described with more particularity in a publication by Owens-Corning Fiberglas Corporation entitled "Textile Fibers For Industry", Pub. No. 5-GT-5442 A, March 1972. A bundle of several hundred filaments are ordinarily twisted to make a strand. The yarn may be one strand, or several strands twisted together. The yarn weight strongly affects the rate of hardening of the cast. For example, a tape made of "150-strand count" yarn hardened about twice as fast as when the yarn was composed of four 150-count strands. Therefore, the 150-strand count yarn is desirable, and it is available with almost any filament diameter.

A tight twist in the strand or yarn is undesirable, because it tends to reduce the space between filaments, and thereby reduce the resin loading.

The geometry of knitting does not affect the porosity of the cast, and therefore, the hardening rate of the cast, provided the impregnated roll is allowed to drain sufficiently. Stretchability, and thus conformability to irregular contours, is affected by the geometry of knitting, but the importance of this is minimal with this cast, because the inherent adhesiveness of the resin solution provides good conformability even with poorly stretchable tapes.

The thermoplastic polymers useful in the orthopedic cast package of the invention include polymethylmethacrylate, polystyrene and other polymers capable of forming concentrated (20%-45% by weight of polymer) solutions of moderate viscosity in non-toxic volatile solvents. Polymethylmethacrylate polymers or resins are polymers of acrylic and methacrylic acids and their esters and are produced in accordance with methods disclosed in U.S. Pat. Nos. 1,937,323 and 1,980,483. Solid grades are preferable having molecular weights ranging from 10,000 to 100,000. Polystyrenes having a molecular weight of 75,000 to 200,000 are also suitable. Such thermoplastic polymers are available commercially from a number of sources and are used primarily in injection molding operations and as coatings.

The non-toxic volatile solvents useful in the orthopedic cast package of the invention include acetone, methylene chloride, ethyl acetate and mixtures thereof, and mixtures of methylene chloride with ethanol or isopropanol. Preferred solvent systems are ternary mixtures of 1,1,2-trifluoro-1,2,2-trichloroethane, methylene chloride and acetone, and mixtures of fluorotrichloromethane, 1,1,2-trifluoro-1,2,2-trichloroethane and acetone. Ethyl acetate is useful with polystyrenes.

The above ternary solvent mixtures dissolve polymethylmethacrylate even though the fluorinated solvents alone do not. Resin solutions containing about 14% acetone or less are "non-flammable", in that no flame propagation occurs when a match flame is held briefly under the wet tape, or under a freshly prepared cast, and no flaming persists upon removal of the match.

Various polymer solutions have been satisfactorily employed with a polymethacrylate polymer such as Acryloid A-11 or Acrylite H-15 as shown in the following Table 1.

This is because the glass tape is knitted from fibers comprising a bundle of very fine filaments, whose surface is highly wettable by resins or resin solutions. Because of the large glass surface area, and the numerous capillaries between glass filaments and fibers, the volume of solution held in capillaries is high. Because capillarity is an equilibrium property, the impregnating solution is not as likely to flow during storage.

The capillary holding capacity of a tape knitted from B filament 150 strand count yarn is illustrated in Table II. To determine these values, rolls of tape were soaked in the liquid, then allowed to drain in a closed environment (to prevent evaporation) for long times. Practically the same volume of fluid was retained, whether it was acetone or a resin solution. It can also be seen that several days, or perhaps weeks, of draining are needed with a 40% solution to reach equilibrium.

TABLE II

| Capillary holding capacity of rolls of Beta knit tape | | | |
|---|---|---|---|
| Retention of fluid after soaking and prolonged draining. | | | |
| Acryloid A-11 resin concentration in acetone (% by weight) | Density of solution (g/ml) | Drainage time (days) | Liquid remaining on roll (ml/g blass)** |
| 0 (acetone only) | 0.790 | 1 | 1.16 |
| 25 | 0.875 | 1 | 1.18 |
| 35 | 0.908 | 17 | 1.26 |
| 40 | 0.935 | 2 | 1.38 |
| 40 | | 5 | 1.28 - 1.32 |
| 40 | | Weeks* | 1.21 |

*Total time was 5 weeks, but because of a vapor leak, the roll dried out sometime during this period.
**The specific weight of Beta knit tape ranges between 19.1 and 20.0 g/ft². To get ml/ft² values, multiply by 19.5.

TABLE I

| Example | Acryloid A-11 | Flame Retardant | Acetone | Methylene Chloride | Ethanol | Isopropanol | CLF$_2$CCFCL$_2$ | CCLF$_2$ | Acrylite H-15 |
|---|---|---|---|---|---|---|---|---|---|
| 1 | 35 | | 65 | | | | | | |
| 2 | 40 | | 60 | | | | | | |
| 3 | 45 | | 55 | | | | | | |
| 4 | 40 | | | 60 | | | | | |
| 5 | 40 | | | 42 | 18 | | | | |
| 6 | 40 | | | 42 | | 18 | | | |
| 7 | 33.3 | | 41 | | | | 25.7 | | |
| 8 | 45 | | 16.5 | 38.5 | | | | | |
| 9 | 36 | | 32 | | | | 32 | | |
| 10 | 32.7 | | 27.3 | | | | 40 | | |
| 11 | 31 | | 28 | | | | 41 | | |
| 12 | 34 | | 31 | | | | 35 | | |
| 13 | 30 | | 20 | 10 | | | 40 | | |
| 14 | 22.1 | 2.0* | 11.9 | | | | 30.8 | 33.3 | |
| 15 | 24.3 | 1.7* | 13 | | | | 30 | 30 | |
| 16 | 29.2 | 1.2* | 13.7 | | | | 40.3 | | |
| 17 | 24.8 | | 13.4 | 15.6 | | | 30.8 | 31 | |
| 18 | 26.1 | 2.9** | 12.6 | | | | 29.2 | 29.2 | |
| 19 | 30.1 | 3.4** | 13.0 | | | | 26.7 | 26.7 | |
| 20 | 28.4 | 3.2** | 12.8 | | | | 27.8 | 27.8 | |
| 21 | | | 60 | | | | | | 40 |

*tris(2,3dibromopropyl)phosphate
**Equal parts of pentabromoethylbenzene and triethyl phosphate In addition to the thermoplastic, flame retardants, plasticizers or other additives may be incorporated into the solution.

The amount of thermoplastic polymer solution having a polymer concentration of about 20 to 45% employed in the orthopedic cast package of this invention is sufficient to provide about 0.8 to 1.5 milliliters of solution per gram of tape.

Although not wishing to be bound by any theory of this invention, it is believed that capillarity rather than viscosity is responsible for retention of the polymer solution on the tape.

Whenever the volume of solution on the roll was close to, or below the capillary hold capacity, casts of good to excellent porosity were obtained. This is understandable, because if all the liquid is held in the capillary spaces within the bundles and at junction points, the open holes in the weave structure must be free of liquid.

Therefore, good porosity can be insured simply by reducing the volume of impregnating solution to a level close to the capillary holding capacity, and allowing any excess to drain away from the roll during storage.

If for the sake of porosity and storage stability, the impregnating volume is restricted to the capillary holding capacity, the resin loading depends only on the concentration of the impregnating solution. For example, the impregnation of "Beta knit", whose capillary holding capacity is about 1.2 ml/g, with 25%, 35%, or 40% Acryloid A-11 resin solutions in acetone, will yield resin loadings of, respectively, 0.26, 0.39, and 0.45 g/g, or about 5, 7.6, and 8.8 g/ft$^2$.

Table III lists the hardening rates and strengths of a number of casts of this invention. From these examples a polymethylmethacrylate content of 7–8 g/ft$^2$ seems as good as at 10–11 g/ft$^2$. The number of layers does not seem to matter in short casts, as long as the total tape area is constant, because the whole cylinder deforms as a unit under load. When the diameter of the cylinder increases, more tape and more layers are needed to achieve the same strength. Strength in this Table III and hereafter is defined as the force needed to reduce the diameter of a cylindrical cast by 1 millimeter.

These casts are only slightly affected by warm water, as long as they are at least a day old. A cast was submerged for 10 minutes in water at 45°–50° C., and its strength was measured. The wet strength was 2.2 kg/mm, compared to the original 2.9 kg/mm. Upon drying, strength increased to 2.6 kg/mm. The cast felt dry to the touch a few minutes after removal from water.

TABLE III

Hardening rate and strength of cylindrical casts

| Tape | | | Cast | | | Time needed to reach | |
|---|---|---|---|---|---|---|---|
| Area (ft$^2$) | Resin loading (g/ft$^2$) | Length (in.) | Inside Diameter (in.) | Average Number of Layers | Ultimate or highest strength (kg/mm) | 1 kg/mm (min.) | 2 kg/mm (min.) |
| 1.31 | 7.9 | 4 | 2¼ | 5½ | 2.9 | 17 | 30 |
| 1.23 | 7.0 | 3½ | 2¼ | 5 | 2.7 | 20 | 34 |
| 1.24 | 7.1 | 3¾ | 2¼ | 4½ | 2.9 | 23 | 45 |
| 1.24 | 10.6 | 3¾ | 2¼ | 4½ | 2.9 | 31 | 45 |
| 1.23 | 10.4 | 4 | 2¼ | 4 | 2.6 | 16 | 33 |
| 1.23 | 11 | 3¾ | 2¼ | 4½ | 2.8 | 30 | 73 |
| 1.20 | 7.8 | 2½ | 3½ | 6 | 1.5 | 45 | — |
| 3.79 | 5.9 | 8½ | 3½ | 5½ | 1.4 | <17 | — |
| 4.38 | 10.3 | 7¾ | 3½ | 7 | 2.9 | 33 | 49 |

The orthopedic cast package of this invention will now be described in referrence to the accompanying drawings wherein:

FIG. 5 is a vertical cross-sectional view of another embodiment of the orthopedic cast package of the invention in final upright positions;

FIG. 6 is a perspective view of the internal support means of the package shown in FIG. 5;

FIG. 7 is a vertical cross-sectional view of still another embodiment of the orthopedic cast package of the invention in final upright position;

FIG. 8 is a partial cross-sectional view taken along line 8—8 of FIG. 7 of the internal support means of the package shown in FIG. 7;

Figure 1:
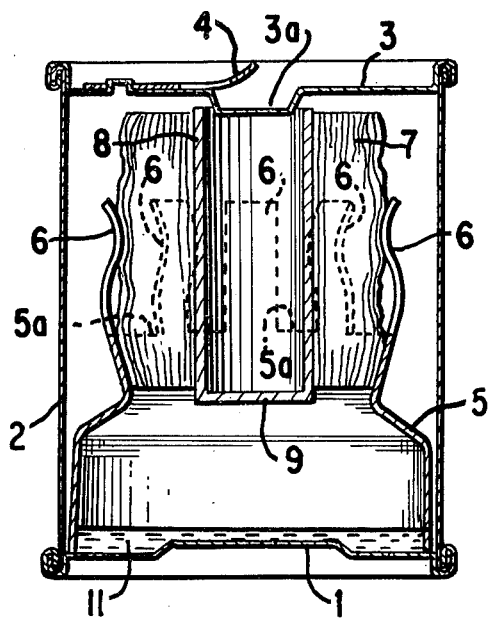
FIG. 1 is a vertical cross-sectional view of a preferred embodiment of the orthopedic cast package of the invention in final upright position.
Figure 4:
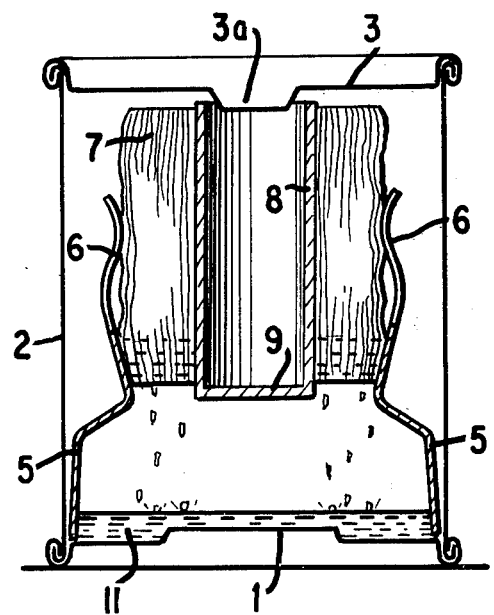
FIG. 4 is a vertical cross-sectional view of the preferred embodiment in upright position after partial drainage of the thermoplastic polymer solution from the orthopedic tape roll.

Turning now to FIG. 1, the orthopedic cast package of the invention includes an outer cylindrical container defined by a bottom wall 1, a peripheral side wall 2 and a top closure 3 with depression 3a and having a pull tab 4 for removal of the entire surface of top closure 3, such as is described for example in U.S. Pat. No. 3,411,661, the disclosure of which is incorporated herein by reference. Situated within the outer cylindrical container is a double funnel-like cylindrical chamber defined by wall 5 and eight equally spaced resilient elongated extensions 6 extending upwardly from the top 5a of wall 5. Mounted within extensions 6 and supported by wall 5 is orthopedic tape roll 7 wound around spool 8 closed at its lower end by wall 9. Orthopedic tape roll 7 is wetted with thermoplastic polymer solution, the excess of which has drained into the lower portion of the outer cylindrical chamber and is designated 11. FIG. 4 is similar to FIG. 1 but shows the thermoplastic polymer solution 11 draining from orthopedic tape roll 7.

Figure 2:
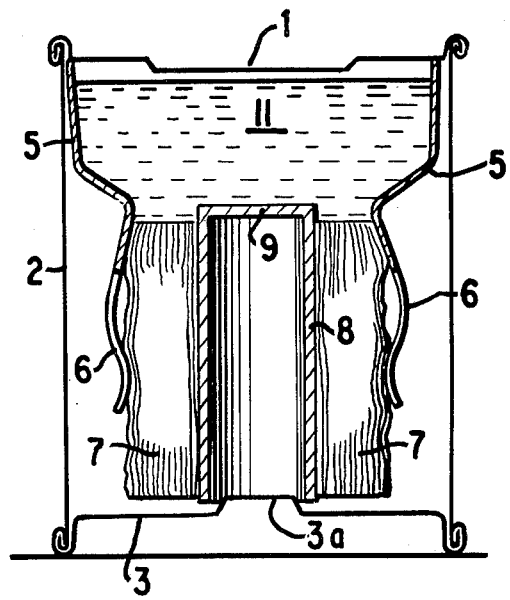
FIG. 2 is a vertical cross-sectional view of the preferred embodiment in inverted position immediately after filling with the thermoplastic polymer solution.

In FIG. 2, the outer cylindrical container is shown in inverted position immediately after filling the funnel-like cylindrical chamber designated by wall 5 with thermoplastic polymer solution designated 11 and sealing into position of bottom wall 1.

Figure 3:
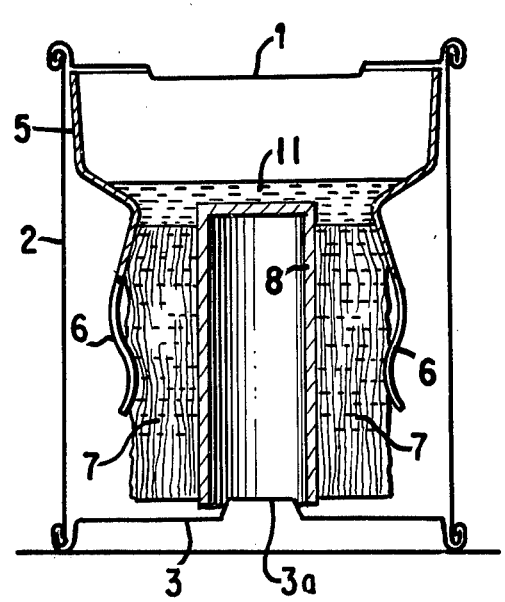
FIG. 3 is a vertical cross-sectional view of the preferred embodiment in inverted position after partial saturation of the orthopedic tape roll with thermoplastic polymer solution.

FIG. 3 is similar to FIG. 2 but shows the thermoplastic polymer solution 11 having partially penetrated orthopedic tape roll 7.

The outer cylindrical container can be fabricated from metal such as tin-plate or aluminum and is available commercially as a three-piece can. The funnel-like cylindrical chamber defined by wall 5 and having integral extensions 6 can be fabricated from a variety of plastic materials insoluble in the thermoplastic polymer solution such as molded polyethylene and polypropylene. Tape spool 8 having closed end 9 can similarly be molded from plastic material.

Although FIGS. 1 through 4 are schematic drawings only, it is evident that the lower end of wall 5 of the funnel-like cylindrical chamber is immediately adjacent to wall 2 of the outer cylindrical container and the upper end of tape spool 8 is immediately adjacent the sides of depression 3a such that the tape roll 7 is maintained in fixed position within the outer cylindrical chamber.

In assembling the orthopedic cast package shown in FIGS. 1 through 4, top wall 3 is first sealed to side wall 2 of the outer cylindrical container and the container is inverted. The tape roll 7 wound on spool 8 is then inserted between extensions 6 and pressed down to within the confines of wall 5 of the funnel-like cylindrical chamber. The tape roll-funnel like chamber assembly is then inverted and placed within the outer cylindrical chamber, the thermoplastic polymer solution is metered into the funnel-like chamber, and bottom wall 1 is sealed into place. The orthopedic cast package is maintained in inverted position as shown in FIG. 2 for at least forty-eight hours until the tape roll 7 is completely wetted with polymer solution. The orthopedic cast package is then turned to its upright position and maintained in its upright position to permit drainage of polymer solution from the tape roll 7. Proper drainage requires at least forty-eight hours after which time the orthopedic cast package is ready for use.

Turning now to FIGS. 5 and 6, another embodiment of the orthopedic cast package is shown having an outer cylindrical container defined by a bottom wall 12 and side wall 13, formed from one piece of stock, and top wall 14, again with a pull tab (not shown). Top wall 14 has depression 15 in its center. Within the container and disposed adjacent bottom wall 12 is ring 16 having affixed thereto support member 17 having surface 18. Suspended on support member 17 is hollow tape spool 19 having orthopedic tape roll 20 wound thereon. Tape roll 20 is held in wound position by tie 21. In this embodiment, the bottom of tape spool 19 rests on surface 18 of support member 17, and the top surface of tape spool 19 is engaged by top depression 15 to maintain the wetted orthopedic tape roll in fixed position. Excess thermoplastic polymer solution is designated 23.

In the embodiment of FIGS. 5 and 6, the tape roll 20 on spool 19 is prewetted with polymer solution in an external bath, placed on support member 17 in the cylindrical container and then top wall 14 is sealed into place.

Turning now to FIGS. 7 and 8, the outer cylindrical container is defined by bottom wall 24, side wall 25 and top wall 26, having depression 27, and a pull tab (not shown). Bottom wall 24 has a cylindrical raised portion 28. Within the outer cylindrical chamber is disposed the funnel-like chamber defined by cylindrical wall 29 having four resilient finger-like extensions 30. Arched member 31 is attached to the inside of wall 29. Wetted orthopedic tape roll 32 wound about tape spool 33 having brace 34 is positioned within extensions 30 such that brace 34 contacts arched member 31 and the bottom of tape roll 32 contacts the inside of wall 29. Also, the bottom of wall 24 is adjacent the perimeter of raised portion 28 and the top of tape spool 33 is adjacent the perimeter of depression 27 such as to hold the tape roll-funnel-like chamber assembly in fixed position within the outer cylindrical chamber. Excess thermoplastic polymer solution is designated as 35.

Figure 9:
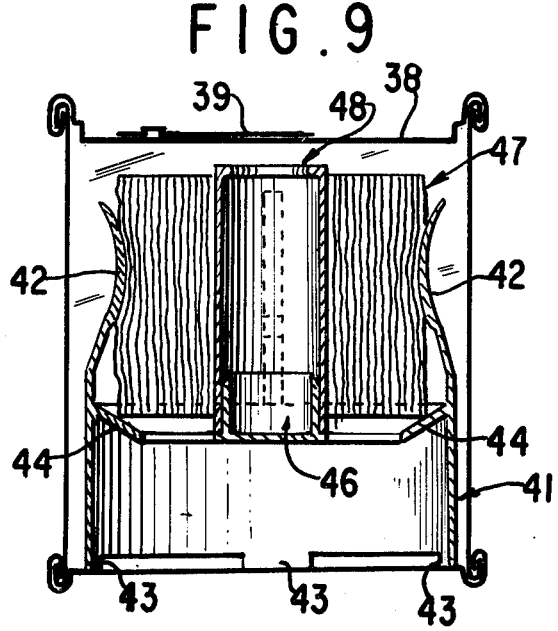
FIG. 9 is a vertical cross-sectional view of another embodiment of the orthopedic cast package of the invention in assembled upright position.
Figure 10:
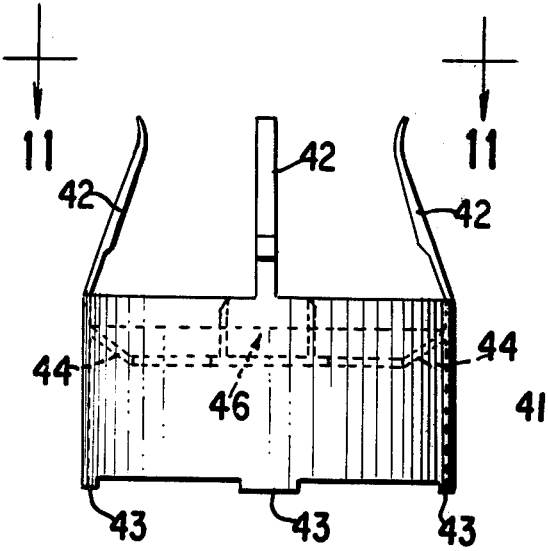
FIG. 10 is a vertical cross-sectional view of the internal support means of the package shown in FIG. 9.
Figure 11:
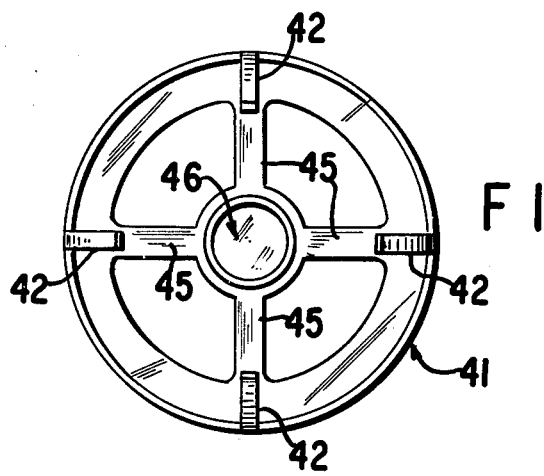
FIG. 11 is a top view along line II—II of FIG. 10.

Turning now to FIGS. 9 to 11, the outer cylindrical chamber is defined by bottom wall 36, side wall 37 and top wall 38 having pull tab 39. Within the outer cylindrical chamber is disposed the funnel-like chamber defined by cylindrical wall 41 having four resilient finger-like extensions 42 and four feet-like extensions 43. Downwardly and inwardly depending from cylindrical wall 41 is conical skirt 44 and extending inwardly from the bottom rim of conical skirt 44 are four support members 45 connected to center plug 46. Wetted orthopedic tape roll 47 wound about tape spool 48 is positioned within extensions 42 such that spool 48 is engaged by plug 46 and tape roll 47 rests on conical skirt 44. As can be seen in FIG. 9, cylindrical wall 41 is spaced adjacent the outer cylindrical chamber and the internal support means is spaced such that the upper end of tape spool 48 is adjacent top wall 38.

The embodiment shown in FIGS. 9 to 11 can be sized to a standard Number 211×304 can with 13 feet of 1.75 inch orthopedic tape wound on a spool.

Figure 12:
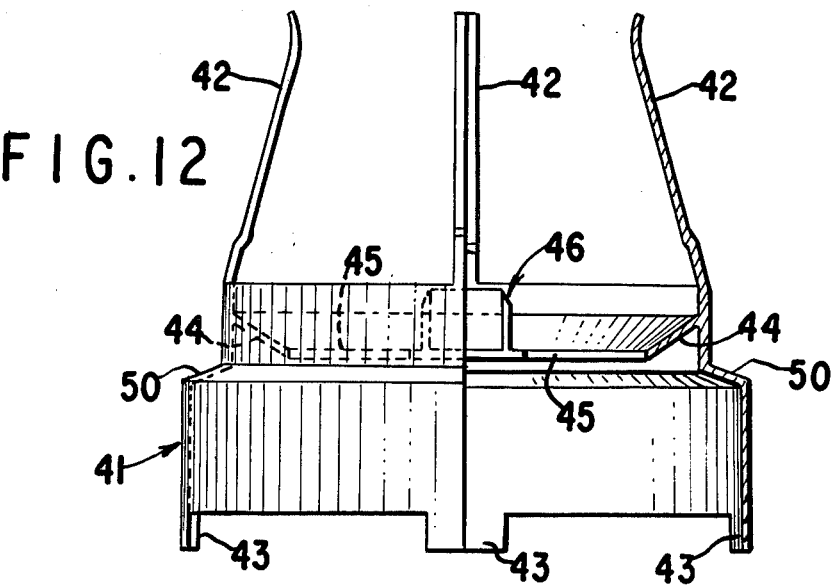
FIG. 12 is a vertical cross-sectional view of an alternative internal support means designed for a larger sized orthopedic tape roll and a larger sized package.

The internal support means shown in FIG. 12 is similar to that shown in FIGS. 10 and 11 except that flange 50 extends cylindrical wall 41 to a larger diameter to accommodate a larger standard size can such as a Number 401×411 can with 23 feet of 2.75 inch orthopedic tape roll wound on a spool.

The orthopedic cast package of this invention can be sized to contain orthopedic tape rolls of 1.75 inch to 6 inch widths or larger, having from 6 to 30 feet of wound tape. The larger the tape size, the more volume must be provided to contain the excess polymer solution after drainage. Also, the larger the tape, the more time must be provided for impregnation of the tape by polymer solution and drainage of the polymer solution from the wetted tape.

I claim:

1. An orthopedic cast package consisting essentially of an outer container having a bottom wall, a peripheral side wall extending upwardly from said bottom wall and providing an open upper end of said container, a closure and associated means for providing a vapor-tight seal on said upper end of said outer container, a hollow-core cylindrical roll of orthopedic tape having closure means for the core at its lower end mounted within said outer container, said tape being of liquid pervious material and said tape roll being supported concentrically with respect to said peripheral side wall of the outer container, the outer diameter of said tape roll being less than the inner diameter of said peripheral side wall and the height of tape roll being less than the height of the peripheral side wall, and means for supporting said tape roll in a spaced relationship away from said bottom wall and concentrically with respect to said peripheral side wall of the outer container, said support means permitting free drainage from the bottom surface of said tape roll, said orthopedic cast package also containing a solution of a thermoplastic polymer in a non-toxic volatile solvent having a polymer concentration of at least about 20% by weight; wherein the supporting means for said tape roll also defines a chamber having an upper section and a lower section, whereby both sections of said chamber meet where the chamber has a diameter less than the diameter of the tape roll and larger than the closed hollow core of the tape roll, said lower section comprising about 20 to about 50% of the internal volume of the outer container.

2. The orthopedic cast package of claim 1 wherein the bottom wall of the outer container is separately attached to the peripheral side wall to provide a vapor-tight seal at the lower end of the outer container.

3. The orthopedic cast package of claim 2 which further includes a cylindrical tape spool upon which the hollow-core cylindrical roll of orthopedic tape is wound, wherein the closure means is integral with the spool.

4. The orthopedic cast package of claim 3 wherein the orthopedic tape material comprises interlaced glass yarns.

5. The orthopedic cast package of claim 4 wherein the diameter of said chamber where the lower section and upper section meet is slightly less than the diameter of the tape roll to engage the lower portion of the tape roll and the upper section of said chamber has a diameter slightly larger than that of the tape roll, and at least two resilient oppositely positioned elongated extensions extending upwardly from the upper section of the chamber further to engage the tape roll and hold it in juxtaposition with the chamber.

6. The orthopedic cast package of claim 5 wherein the thermoplastic polymer is selected from polymethylmethacrylate and polystryene and the non-toxic volatile solvent is selected from the class consisting the acetone, methylene chloride, ethyl acetate or mixtures thereof, mixtures of methylene chloride with ethanol and isopropanol, mixtures of 1,1,2-trifluoro-1,2,2-trichloroethane, methylene chloride and acetone, and mixtures of fluorotrichloromethane, 1,1,2-trifluoro-1,2,2-trichloroethane and acetone.

7. The orthopedic cast package of claim 2 which further includes a cylindrical tape spool upon which the hollow-core cylindrical roll of orthopedic tape is wound.

8. The orthopedic cast package of claim 7 wherein the orthopedic tape material comprises interlaced glass yarns.

9. The orthopedic cast package of claim 8 wherein the support means includes the closure means for the lower end of the hollow core of the tape spool.

10. The orthopedic cast package of claim 9 wherein the diameter of the chamber where both sections of said chamber meet is defined by a downwardly and inwardly depending conical skirt for supporting the tape roll.

11. The orthopedic cast package of claim 10 wherein the smaller diameter of the conical skirt of said chamber where the lower section and upper section meet is slightly less than the outer diameter of the tape roll to engage the lower portion of the tape roll and the upper section of said chamber has a diameter slightly larger than that of the tape roll, and at least two resilient oppositely positioned elongated extensions extending upwardly from the upper section of the chamber further to engage the tape roll and hold it in juxtaposition with the chamber, and support members extending inwardly from the inner edge of the conical skirt for supporting the closure means for the lower end of the hollow core of the tape spool.

12. The orthopedic cast package of claim 11 wherein the thermoplastic polymer is selected from polymethylmethacrylate and polystyrene and the non-toxic volatile solvent is selected from the class consisting of acetone, methylene chloride, ethyl acetate or mixtures thereof, mixtures of methylene chloride with ethanol and isopropanol, mixtures of 1,1,2-trifluoro-1,2,2-trichloroethane, methylene chloride and acetone, and mixtures of fluorotrichloromethane, 1,1,2-trifluoro-1,2,2-trichloroethane and acetone.

13. The orthopedic cast package of claim 1 wherein the orthopedic tape material comprises interlaced glass yarns.

14. The orthopedic cast package of claim 13 wherein the thermoplastic polymer is selected from polymethylmethacrylate and polystyrene and the non-toxic volatile solvent is selected from the class consisting of acetone, methylene chloride, ethyl acetate or mixtures thereof, mixtures of methylene chloride with ethanol and isopropanol, mixtures of 1,1,2-trifluoro-1,2,2-trichloroethane, methylene chloride and acetone, and mixtures of fluorotrichloromethane, 1,1,2-trifluoro-1,2,2-trichloroethane and acetone.

* * * * *